United States Patent

Konyári et al.

[11] Patent Number: 5,374,771
[45] Date of Patent: Dec. 20, 1994

[54] PROCESS FOR THE PREPARATION OF HIGH-PURITY DEFEROXAMINE SALTS

[75] Inventors: Zoltán Konyári; Vilmos Kéri; Antal Kovács; Sándor Horkay; László Eszenyi; János Erdélyi; Ilona Himesi, all of Debrecen; György Toth, Nyiregyhaza; János Bálint, Debrecen; Judit Szilávi, Debrecen; Ferenc Vinczi, Debrecen; Csaba Szabó, Debrecen; Nelli Sas, Debrecen, all of Hungary

[73] Assignee: Biogal Gyogyszergyar Rt., Debrecenn, Hungary

[21] Appl. No.: 67,815

[22] Filed: May 27, 1993

[30] Foreign Application Priority Data

Jun. 1, 1992 [HU] Hungary ............... P9201811

[51] Int. Cl.$^5$ ............................ C07C 303/32
[52] U.S. Cl. ........................ 562/114; 562/623
[58] Field of Search ................. 562/114, 623

[56] References Cited

U.S. PATENT DOCUMENTS

| | | | |
|---|---|---|---|
| 3,471,476 | 10/1969 | Goeumann et al. | 260/239.3 |
| 3,852,424 | 12/1974 | Gaeumann et al. | 424/118 |
| 4,419,365 | 12/1983 | McLachlan | 424/320 |
| 4,704,274 | 11/1987 | Sakuma et al. | 424/88 |
| 5,235,037 | 8/1993 | Krishnan | 530/322 |

FOREIGN PATENT DOCUMENTS 0616139 10/1962 Belgium.
0619532 12/1962 Belgium.
0999583 7/1965 United Kingdom ............ 562/623

OTHER PUBLICATIONS

CA84(13): 87982c (1971.

Primary Examiner—José G. Dees
Assistant Examiner—Barbara S. Frazier
Attorney, Agent, or Firm—Keil & Weinkauf

[57] ABSTRACT

A process for the preparation of high-purity deferoxamine salts from filtered fermentation liquors containing deferoxamine B as active ingredient by the adsorption of the active ingredient onto an ion exchange resin and the subsequent dissolution and purification thereof, which comprises carrying out the separation of the deferoxamine salt subsequent to the concentration of the eluate by salting out from an aqueous solution or from a mixture of water and an organic solvent and purifying it by repeated salting out and/or by methods known per se, and optionally a) preparing the methanesulfonate salt by known methods, or b) passing the aqueous solution of the deferoxamine salt trough an ion exchange resin containing methanesulfonate anions as counter ions and recovering the methanesulfonate salt from the effluent, preferably by lyophilization.

6 Claims, No Drawings

PROCESS FOR THE PREPARATION OF HIGH-PURITY DEFEROXAMINE SALTS

This invention relates to a process for the preparation of high-purity deferoxamine salts, preferably the methanesulfonate salt, from filtered fermentation liquors containing deferoxamine B as active ingredient.

Among the great number of deferoxamines known from the literature deferoxamine B is the most valuable one, which is a selective iron mobilisator and can be used in the therapy for the treatment of different anaemiae and iron intoxications.

For the industrial scale production of deferoxamine B the Streptomyces pilosus strain is applied, which produces mostly deferoxamine B in a culture medium poor in iron (Belgian patent specification No. 619,532).

In the course of the preparation of pure deferoxamine B ingredient a solution of 8-hydroxychinoline in methanol is added to the fermentation liquor in order to decompose the ferrioxamine complex formed by the iron-(III) ions of the culture medium with deferoxamine. The fermentation liquor is then filtered and the excess of 8-hydroxychinoline is removed from the filtered liquor with the aid of AMBERLITE IR-45 ion exchange resin. The active ingredient is adsorbed by AMBERLITE IRC-50 ion exchange resin and eluted with 0.2M hydrochloric acid. Thus a great volume of diluted eluate is obtained. In order to concentrate and purify the active ingredient in the eluate the solution is extracted at pH 5 with benzyl alcohol or with a 1:1 mixture of chloroform and phenol. The extract is treated again with 8-hydroxychinoline, methyl isobutyl ketone is added to it and the mixture is re-extracted with water. The excess of 8-hydroxychinoline is removed by extraction with chloroform. In order to isolate deferoxamine B hydrochloride the aqueous solution is concentrated in vacuo and the separated crystals are recrystallized from the mixtures of water and methanol and water and acetone (Belgian patent specification No. 619,532).

From the foregoing it can be seen that the recovery procedure is rather cumbersome. For the extraction three different organic solvents are used on three occasions, for the recrystallization two different solvents are applied. Separating the solvents, returning them back to the recovery procedure, removing the contaminations accumulated in the solvent phase, treating the wastematerials are all problematical operations rendering the technological process cumbersome.

Deferoxamine B is generally used in the form of the methanesulfonate salt which is readily soluble in water. The methanesulfonate is prepared from deferoxamine B hydrochloride in such a manner that an aqueous solution of the latter is passed through an anion exchange resin in the hydroxyl form to be converted first to base, then a solution containing an equivalent amount of methanesulfonic acid is added to the aqueous solution of the deferoxamine B base. The solution is evaporated and the thus-obtained deferoxamine B methanesulfonate is recrystallized from an aqueous alcohol or from an aqueous mixture of methanol and acetone (Belgian patent specification No. 616,139).

The present invention aims at providing a process for the preparation of high-purity deferoxamine B salts, especially the methanesulfonate, from fermentation liquors containing deferoxamine B as active ingredient, which process can be carried out more readily and more economically than the hitherto known processes.

The invention is based on the recognition that deferoxamine salts, and especially the hydrochloride, can be separated by salting out from aqueous solutions or from mixtures of water and organic solvents. According to our experiences during the isolation of the active ingredient, after the ion exchange of the filtered fermentation liquor and the subsequent concentration of the eluate containing the active ingredient, deferoxamine B hydrochloride can be separated directly by salting out operation. By this means the extraction with an organic solvent and the re-extraction specified above can be eliminated from the working up procedure of the fermentation liquor. The thus-obtained crude deferoxamine B hydrochloride can be purified by repeating the salting out procedure or by any other known method, such as recrystallization, repeated ion exchange etc. So the application of salting out renders the recovery process much simpler and much more economical.

It has also been recognized that the preparation of deferoxamine B methanesulfonate in a quality suitable for pharmaceutical purposes can be accomplished readily from a pure deferoxamine B salt, preferably from the hydrochloride, by passing a concentrated aqueous solution of the salt through a weakly basic anion exchange resin in the methanesulfonate form and by lyophilizing the solution containing the methanesulfonate salt of deferoxamine B. This method is particularly preferable, since both the preparation of the rather labile deferoxamine B base and the salt formation starting from the latter compound are eliminated. Besides, the separation of the methanesulfonate salt by concentrating a diluted solution thereof and the recrystallization are also eliminated, as deferoxamine B hydrochloride isolated and purified according to the method of invention is so pure that the effluent of the ion exchange containing deferoxamine B methanesulfonate can be directly lyophilized.

During our experiments fermentation liquors cultured by a Streptomyces 101/87 strain (deposition number: MIMNG 1143) containing deferoxamine B as active ingredient were processed.

The fermentation liquor is filtered at an acidic or neutral pH, in order to avoid the decomposition of the active ingredient at a weakly acidic pH, in the presence of sulfate and/or chloride salts. For this purpose preferably ammonium chloride is applied.

From the filtered liquor deferoxamine is bound to a weakly acidic cation exchange resin in the hydrogen form. According to our experiences the adsorptive capacity of the resin can be enhanced by ensuring conditions suitable to decrease the amount of the contaminations bound to the resin. This can be achieved by filtering the fermentation liquor at a weakly acidic pH as specified above and diluting the filtered liquor. It is even more preferable to keep the pH of the filtered liquor at a value between 5 and 8 with a buffer solution, preferably with ammonium acetate or ammonium chloride.

The purifying effect of the ion exchange method can be enhanced by using a forerun column containing an weakly acidic cation exchange resin in the ammonium form unable to adsorb deferoxamine in order to bind a part of the contaminations being present in the filtered liquor.

After the ion exchange the active ingredient may be eluted at a wide pH range of 2 to 12 related to the pH value of the eluate, but it is preferable to carry out the elution with a diluted alkaline solution, e.g. 0.05 to 1.5M sodium hydroxide or ammonium hydroxide solution. During the elution carried out at an alkaline pH value a considerable part of the contaminations gets off the column prior to the appearance of the fractions containing the active ingredient, and the latter is obtained— compared to the filtered liquor—concentratedly.

The decomposition of the active ingredient can be prevented by applying a low temperature (0°–5° C.). It is also preferable to carry out gradient elution.

Prior to the separation of deferoxamine B the eluate is adjusted to neutral or to a weakly acidic pH with an acid, preferably with diluted hydrochloric acid, and concentrated mildly, e.g. by evaporation in vacuo or hyper filtration. The crude deferoxamine B salt is separated from the aqueous concentrate by salting out procedure and cooling. For the salting out preferably ammonium chloride or ammonium sulfate is used.

The purification of the crude product obtained as specified above can be carried out by several methods, e.g. by repeating the salting out operation from an aqueous solution or by recrystallizing the substance from the mixture of water and an alcohol. If the latter method is applied, the efficiency of the recrystallization can be improved by the addition of ammonium chloride to the mixture. In order to remove the concomitant colouring agents and other contaminations sorbents, such as silica gel or activated carbon, or a cation exchange resin, preferably a weakly acidic cation exchange resin in the hydrogen form may be applied. The purification can be accomplished at high efficiency by carrying out repeated salting out from an aqueous solution or from a solution in a mixture of water and an alcohol.

By the above-specified operations and purification methods high-purity deferoxamine salts, e.g. pure deferoxamine B hydrochloride are obtained, which can be converted into the methanesulfonate directly, without any further purification, by dissolving it in water and transferring the solution to an ion exchange resin containing methane- sulfonate counter ions. If the crude deferoxamine B hydro- chloride is purified by ion exchange method, the effluent containing the active ingredient can be transferred directly, after the pH has been adjusted, to an ion exchange resin in the methanesulfonate form.

The anion exchange operation is carried out by using a weakly basic anion exchange resin, and in order to avoid the decomposition of the deferoxamine B methanesulfonate under cooling, preferably at a temperature between 5° C. and 10° C. The active ingredient can be isolated from the solution by lyophilization.

An advantage of the process according to the present invention resides in the fact that the desired deferoxamine B methanesulfonate is obtained from a pure deferoxamine salt in one step, without converting it to base. By this means both the preparation of the barely water-soluble base liable to decomposition and the salt formation from the thus-obtained diluted solution can be eliminated.

A further advantage of the process according to the invention is that no solvent is used for the isolation and purification of the active ingredient either during the crystallization from water based on salting out or during the recrystallization from water. The extraction operations are eliminated, consequently the recovery procedure is economic, simple and safe, furthermore the active ingredient can be isolated from the fermentation liquor in high purity and at good efficiency.

The invention is further illustrated by the following Examples of non-limiting character. The fermentation liquors processed according to the Examples were cultured by a Streptomyces 101/87 strain (deposition number: MIMNG 1143).

EXAMPLE 1

250 kg of fermentation liquor (active ingredient content: 800 g) were adjusted to a pH value between 5.8 and 6.2 with sulfuric acid. The fermentation liquor was filtered through a perlite forelayer under washing with water. The thus-obtained 450 kg of filtered liquor were passed through first 12.6 l of LEWATIT CNP 80 resin in the ammonium form then 28 l of AMBERLITE IRC 50 resin in the hydrogen form. The resins were washed with water and active ingredient was eluted with 0.3M ammonia solution at 0° to 5° C. The fraction of the eluate containing the active ingredient contained 679 g of deferoxamine B representing a yield of 85% related to the fermentation liquor. The 76 l volume of the fraction was adjusted to pH 6.0 to 6.3 with diluted hydrochloric acid and concentrated mildly to a tenth of its original volume. Then 700 g of ammonium chloride were added to the concentrate, and after complete dissolution the mixture was crystallized under cooling to obtain 877 g of crude deferoxamine B hydrochloride, which was recrystallized from a 1:4 mixture of water and methanol, dried and dissolved in the form of 5% aqueous solution, treated in portions with a total amount of 37 g of activated carbon and passed through first 400 ml of AMBERLITE IRC 50 resin in the hydrogen form then 400 ml of AMBERLITE IRA 900 resin in the chloride form. The thus-obtained solution was concentrated indulgently to a concentration of 20% and deferoxamine B hydrochloride was separated at −10° C. after the addition of a four-fold volume of methanol, filtered and dried. Thus 385 g of hydrochloride salt suitable for the formation of methanesulfonate salt were obtained. Active ingredient content determined by photometric method: 99.8%.

From the pure deferoxamine B hydrochloride salt 5% aqueous solution was prepared, which was cooled to 5° C. and passed through 1400 ml of Amberlite IRA 68 resin in the methanesulfonate form. The thus-obtained solution was then subjected to lyophilization to obtain 396 g of deferoxamine B methanesulfonate. Active ingredient content determined by photometric method: 99.5%.

EXAMPLE 2

To 8000 ml of filtered liquor obtained according to Example 1.28 g of ammonium acetate were added. After the dissolution was complete the filtered liquor was passed through 700 ml of AMBERLITE IRC 50 resin in the hydrogen form. The mixture was washed with water, eluted with 1M ammonia solution to obtain 1100 ml of main fraction containing 23 g of deferoxamine B representing a yield of 90% related to the fermentation liquor. The eluate was adjusted to pH 6.0–6.2 with 1M hydrochloric acid and concentrated in vacuo to a fifth of its original volume. The concentrate was cooled to 5° C., the separated substance was filtered in 24 hours and dried. Thus 30 g of crude deferoxamine B hydrochloride were obtained, which were then dissolved in 250 ml of a 1:4 mixture of water and methanol and the solution was treated with 1.3 g of carbon. The clarified solution was kept at −10° C. for 24 hours, the separated deferoxamine B hydrochloride was filtered, washed with a slight amount of the solvent mixture and dried. The thus-obtained 18.8 g of deferoxamine B hydrochloride were dissolved in 290 ml of deionized water, passed through 10 ml of VARION KCO resin in the hydrogen form and the resin was washed with 10 ml of deionized water. The solution was adjusted to pH 5.5 with VARION ADM resin in the hydroxyl form, filtered, cooled to 2° C. and passed through 70 ml of AMBERLITE IRA 68 resin in the methanesulfonate form. The fractions of the ion exchange effluate containing deferoxamine B methanesulfonate were combined, filtered and subjected to lyophilization. Thus 18 g of deferoxamine B methanesulfonate were obtained. Active ingredient content determined by photometric method: 99.4%.

EXAMPLE 3

Pure deferoxamine B hydrochloride containing 75 g of active ingredient was dissolved into 1100 ml of deionized water at 40° C., under stirring. The solution was then cooled to 5° C. and transferred at a flow rate of 150 ml/hour to a fix bed of 300 ml of AMBERLITE IRA 68 anion exchange resin in the methanesulfonate form packed in a column. After the ion exchange the resin was washed with 200 ml of pre-cooled, deionized water. The fractions were combined, the thus-obtained solution was filtered fibre-free and lyophilized. Thus 86 g of deferoxamine B methanesulfonate were obtained. Active ingredient content determined by photometric method: 99.5%. The efficiency of the preparation is 97% related to the pure hydrochloride.

EXAMPLE 4

660 g of crude deferoxamine B hydrochloride obtained according to Example 1 were suspended in 990 ml of 20% ammonium chloride at 5° C. The suspension was kept at the same temperature for 24 hours and filtered. The thus-obtained nutsch-wet product was dissolved in 1300 ml of deionized water at 60° C. After complete dissolution the solution was cooled to 5° C. and the separated substance was filtered in 48 hours. The thus-obtained wet deferoxamine B hydrochloride was dissolved in 2000 ml of a 1:3 mixture of water and methanol at 45° C. and cooled to −10° C. The separated product was filtered in 24 hours and dried in vacuum exsiccator. Thus 195 g of pure deferoxamine B hydrochloride were obtained. Active ingredient content determined by photometric method.: 99.6%.

EXAMPLE 5

25 kg of fermentation liquor were adjusted to a pH value between 6.0 and 6.3 with 1M hydrochloric acid and the fermentation liquor was filtered. The filtered liquor was passed through 3 l of LEWATIT CNP 80 resin at a flow rate of 4.5 l/hour. After the ion exchange the resin was washed with 6 l of deionized water. The active ingredient was eluted with 0.2M hydrochloric acid. The thus-obtained 30 l of eluate was adjusted to a pH value between 5.0 and 5.2 and concentrated to 500 ml. To the concentrate 500 ml of methanol and 30 g of ammonium chloride were added under stirring. The mixture was cooled to 0° C. and allowed to stand for 24 hours. After filtration and drying a crude product containing 59 g of active ingredient was obtained.

EXAMPLE 6

The active ingredient content of 5 kg of filtered fermentation liquor was bound to 550 ml of AMBERLITE IRC 50 resin in the hydrogen form, then eluted with 0.5M ammonia solution. The active eluate (1.4 l) was adjusted to a pH value between 5.5 and 5.7 with a diluted sulfuric acid solution, the elute was evaporated to 100 ml and cooled to 5° C. under stirring. The mixture was allowed to stand for 24 hours, the separated product was filtered and dried. Thus 14.4 g of crude deferoxamine sulfate were obtained in a purity of 66%.

From the crude product pure deferoxamine sulfate was prepared according to the method specified in Example 4, with the difference that the salting out was carried out with ammonium sulfate. The deferoxamine sulfate salt was converted to 6.5 g of pure deferoxamine B methanesulfonate according to the method specified in Example 3. Active ingredient content determined by photometric method: 99.4 %.

What we claim is:

1. A process for the preparation of high-purity deferoxamine salts from filtered fermentation liquors containing deferoxamine B as active ingredient, which comprises adsorbing the active ingredient onto an ion-exchange resin, eluting said active ingredient from the resin, concentrating said eluate by salting out from an aqueous solution, or from a mixture of water and an organic solvent, and purifying said active ingredient.

2. A process as defined in claim 1, which comprises keeping the pH of the filtered liquor prior to the ion exchange at a value between 5 and 8 with a buffer solution.

3. A process as defined in claim 1, which comprises carrying out the elution with 0.05 to 1.5M ammonia or sodium hydroxide solution.

4. A process as defined in claim 1, wherein the organic solvent is selected from the group consisting of methanol, ethanol and acetone.

5. A process as defined in claim 1, which comprises carrying out the methanesulfonate salt formation by ion exchange method at a temperature below 25° C., under cooling.

6. The process of claim 1, wherein the purified active ingredient is passed through an ion-exchange resin containing methanesulfonate anions as counter ions and thereafter recovering the methanesulfonate salt that is formed.

* * * * *

UNITED STATES PATENT AND TRADEMARK OFFICE
CERTIFICATE OF CORRECTION

PATENT NO. : 5,374,771
DATED : December 20, 1994
INVENTOR(S) : KONYARI et al

It is certified that error appears in the above-indentified patent and that said Letters Patent is hereby corrected as shown below:

On the title page, item [75], the tenth inventor's last name should be --Szilágyi--.

Signed and Sealed this

Second Day of May, 1995

Attest:

BRUCE LEHMAN

*Attesting Officer*      *Commissioner of Patents and Trademarks*